United States Patent [19]

Brooks

[11] 3,963,029

[45] June 15, 1976

[54] DIAPER PACKAGE

[75] Inventor: William Victor Hayes Brooks, Toronto, Canada

[73] Assignee: Domtar Limited, Montreal, Canada

[22] Filed: July 12, 1974

[21] Appl. No.: 487,863

[52] U.S. Cl. .............................................. 128/287
[51] Int. Cl.² ........................................ A61F 13/16
[58] Field of Search .................... 128/82, 155–157, 128/268, 284, 286, 287, 289, 290 R, 290 W, 290 H, 290 PB, 292, 296; 206/438, 440

[56] References Cited
UNITED STATES PATENTS

| 2,024,145 | 4/1931 | Cline | 128/290 R |
| 2,145,137 | 1/1939 | Sayers | 128/284 |
| 2,570,011 | 10/1951 | Stamberger | 128/287 |
| 3,585,998 | 6/1971 | Hayford et al. | 128/287 |
| 3,783,869 | 1/1974 | Schnipper | 128/290 |
| 3,783,871 | 1/1974 | Sabee | 128/287 |

*Primary Examiner*—John D. Yasko
*Attorney, Agent, or Firm*—C. A. Rowley

[57] ABSTRACT

A diaper structure folded into a substantially impervious package to impair the escape of vapors therefrom.

6 Claims, 8 Drawing Figures

3,963,029

DIAPER PACKAGE

FIELD OF THE INVENTION

The present invention relates to a diaper. More specifically, the present invention relates to a folded diaper structure to impair the escape of vapors (such as essences or medicaments or the like incorporated into a diaper structure) and to a method of disposing of a used diaper.

DESCRIPTION OF THE PRIOR ART

Disposable diapers having a water-impermeable backing sheet and a substantially hydrophobic water penetrable facing layer with an absorbent pad sandwiched therebetween are well known. One of the more commercially successful of such diapers is folded into a box pleat and is provided with tack points in the crotch area to prevent opening of the box pleats in this area and thereby to provide a narrow crotch section when the girth encircling portions of the diaper are expanded. Such a diaper is described in Canadian Pat. No. 806,856 issued Feb. 25, 1969 to Duncan et al.

It has been suggested to incorporate essences or the like into the diaper to provide a pleasing fragrance to the diaper. Also materials such as medicaments or the like are sometimes incorporated in the diaper for application to the infant when the diaper is worn. Many of these substances vaporize and thus may be lost over a period of time unless some precautions are taken to prevent the loss of these materials.

With the box pleated diaper structure above described, the porous facing material is readily exposed to the atmosphere thereby facilitating evaporation of incorporated substances.

It is contemplated that the facing sheet of the diaper may be coated with a medication such as a salve or the like that may be messy if touched during storage or application of the diaper and thus it is important that the facing sheet not be exposed.

It is thus one of the objects of the present invention to provide a folded diaper structure wherein the porous facing layer or surface of the diaper is not exposed, i.e. a folded diaper structure having its exposed surface composed solely of imperforate plastic backing material.

It is sometimes recommended to remove the pad structure from the diaper facing and backing sheets after use and to flush the pad down the toilet. This leaves only the facing sheet and backing sheet to be disposed of. The main reason for flushing the padding down the toilet is to eliminate the major source of odour from absorbed urine as no adequate and simple method of closing the used diaper to enclose the facing and substantially impair the escape of odor from the used diaper has been devised. U.S. Pat. No. 3,620,217 issued Nov. 16, 1971 teaches a method of folding a used diaper but leaves a good portion of the facing sheet exposed.

It is thus the further object of the present invention to provide a system of folding a diaper to permit temporary storage of the used and folded diaper without creating undue odor problems and thereby facilitate disposal of the used diaper.

SUMMARY OF THE INVENTION

Broadly, the present invention relates to a disposable diaper structure formed by a plastic backing sheet and a hydrophobic porous facing sheet with an absorbent pad therebetween, a vaporizable substance incorporated in said structure, said structure being divided by at least a pair of longitudinally extending folds into a central section and a pair of lateral wing sections. One of the said pair of lateral wing sections being folded into face-to-face relationship with said centre portion and the other of said pair of lateral wing sections being folded over onto said one lateral wing section thereby to completely enclose said facing sheet and leave only said plastic backing sheet exposed.

The present invention further relates to a method of disposing of a diaper having a porous facing sheet and an imperforate backing sheet and preferably provided with securing or tape fasteners for securing the diaper to the infant, the tape fasteners being connected at one longitudinal end and at each lateral edge of the diaper, said method comprising opening the diaper into substantially flat form, folding said diaper upon itself along lines substantially transverse of the diaper with said facing sheet on the inside thereby to form a diaper strip of several thicknesses of the diaper structure, wherein the exposed surface of said strip is formed solely of said backing sheet and in the preferred arrangement with said tabs projecting one from each end thereof; folding the diaper strip upon itself from one end formed by a side edge of the diaper structure toward the opposite end to form a rolled bundle and in the preferred method securing the exposed tab end to the diaper backing to secure the diaper in bundle or packaged form.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
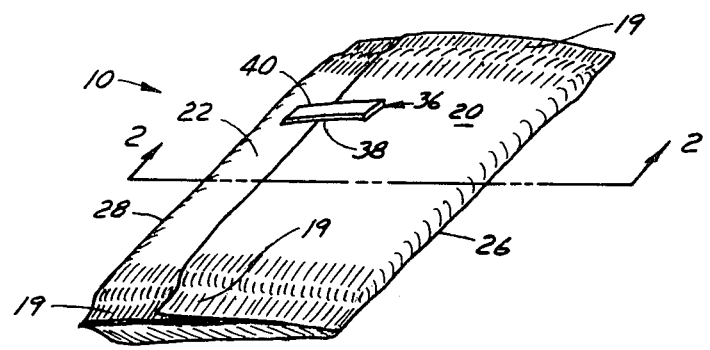
FIG. 1 is an isometric view of one form of diaper structure folded in accordance with the present invention.
Figure 2:
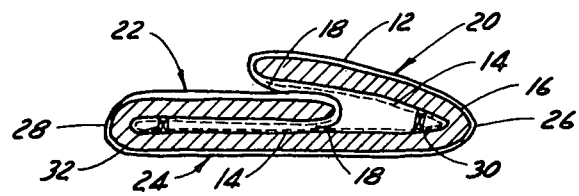
FIG. 2 is a schematic section along the line 2—2 of FIG. 1.

Referring to FIGS. 1 and 2, the diaper structure 10 comprises a substantially water impermeable plastic backing sheet 12 and a porous hydrophobic facing sheet 14 with an absorbent pad 16 trapped therebetween. In the illustrated arrangement, the facing sheet 14 terminates between the folded-over flap 18 of the backing sheet 12, however, if desired, the facing sheet may be positioned on the opposite side of this folded-over flap 18. Preferably, the flap 18 will always be folded over the pad 16 to enclose the side edges of the pad 16. The longitudinal ends of the pad 16 are spaced inward of the longitudinal ends of the sheets 12 and 14 and the projecting end sections of the sheets 12 and 14 are secured together in these areas as indicated at 19.

In the FIG. 1 and 2 arrangements, wing sections 20 and 22 and a central section 24 are formed by longitudinally extending folds 26 and 28 which form the lateral extremities of the folded diaper. The wing sections 20 and 22 are secured to the central section 24 in the crotch area of the diaper by means of tack points 30 and 32 which prevent the wing sections from being completely opened in the crotch section when the diaper is applied to the baby, thereby providing a narrow crotch section in the diaper as applied.

As shown in FIG. 2 of the wing sections, the section 22 in the illustrated embodiment is folded into face-to-face relationship with the central section 24 so that the facing sheet 14 on the wing section 22 is in face-to-face relationship with the facing sheet 14 on the central section 24. The other wing section 20 is folded into overlying relationship with the wing section 22 in the manner illustrated. It will be seen from FIG. 1 and 2 that when the diaper is folded as illustrated the only material exposed is the plastic backing sheet 12, i.e. the folded-over section 18 at the side edges of the wing section 20 contacts the backing sheet 12 on the wing section 22 and substantially seals the diaper, thereby permitting little if any vapor to escape from the sides of the diaper. Escape of vapor on the longitudinal ends of the diaper is inhibited by the fact that the pad 16 terminates short of the longitudinal ends of the diaper and the facing and backing sheets 12 and 14 are directly secured together in these areas 19.

Figure 3:
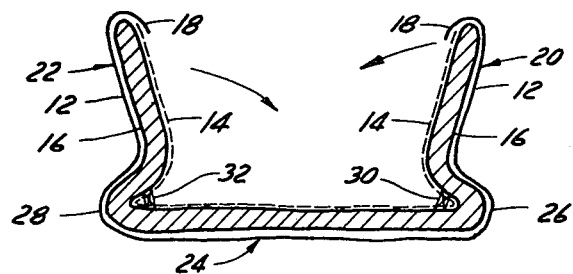
FIGS. 3 and 4 illustrate one mode of closing the diaper after use.

The sealed structure illustrated in FIG. 1 and 2 substantially prevents ambient air from penetrating the folded diaper whereby essence material or vaporizable medicament or the like incorporated in the diaper, for example by impregnation into the pad 16 or by coating on the facing sheet 14, has little opportunity to be dissipated until after the diaper is opened (i.e. opened to the position shown in FIG. 3). Thus with this folded diaper structure the dissipation of incorporated vaporizable materials prior to use is substantially eliminated.

When the facing sheet 14 is positioned on the opposite side of the folded-over section 18 of the backing sheet 12 the efficiency of the folded structure may be slightly reduced due to the poorer seal between the folded section 18 on the wing section 20 and the backing sheet 12 on the wing section 22. However, it still impairs dissipation of vaporizable substances in the in the diaper.

Figure 2A:
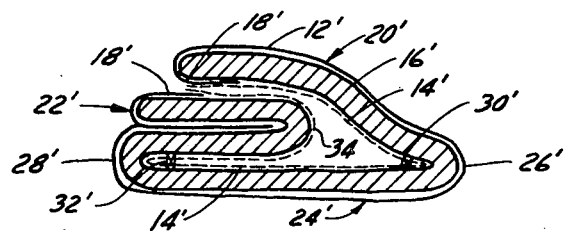
FIG. 2a is a schematical section similar to FIG. 2 but showing a modified folding arrangement.

A modified folded diaper is illustrated in FIG. 2a. In the FIG. 2a arrangement, like parts to those shown in FIG. 2 have been designated by the same reference numeral followed by a prime ('). In FIG. 2a, wing sections 20' and 22' and the central section 24' are of slightly different widths than the equivalent sections shown in FIG. 2.

In the FIG. 2a arrangement, the section 22' is folded over to face-to-face relationship with the section 24' in the same manner as illustrated in FIG. 2 but is further folded back upon itself on fold 34 to form a pleat. The wing section 20' is folded on fold line 26' into overlying relationship with the central section 24' and with the other wing section 22'. The folded-over section 18' at the free side edge of the wing section 20' lies in face-to-face relationship with the folded-over section 18' on the wing section 22' to substantially seal the diaper in the same manner as it was sealed in the FIG. 2 embodiment.

In the preferred form of diaper, a pair of securing tabs or tape fasteners 36 will be provided at opposite lateral or side edges and adjacent one longitudinal end edge of the diaper to eliminate the need for pins and to facilitate securing the diaper onto the infant and also to facilitate closing the diaper after use.

Each of the fasteners 36 is firmly secured to the backing sheet 12 or 12' by its attached end 38 while its free end 40 is provided with a pressure sensitive adhesive coating that normally is protected by a release sheet not shown that is stripped from the end 40 when the fastener 36 is to be used.

Figure 4:
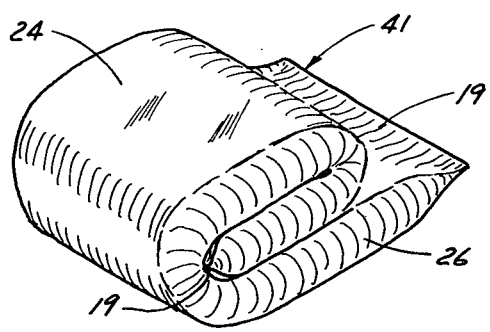

After the diaper has been used, it must be disposed of. FIG. 3 and 4 illustrate one mode of the folding of the diaper of FIG. 2 for disposal. In this mode of disposal, preferably the feces are first removed or dropped from the diaper into the toilet although this is not absolutely essential. The used diaper is then folded as follows: one of the wing sections, say wing section 22, is folded into face-to-face relationship with the upper surface of the central section 24 followed by folding of the section 20 onto section 22 so that the diaper in cross section at this point will look essentially the same as shown in FIG. 2. The diaper is then rolled upon itself in the manner illustrated in FIG. 4 so that one of the longitudinal end edges 19 is rolled inside of the diaper thereby to form a used diaper package 41. If desired, the diaper may be secured in the position by an elastic band or the like or a suitable strip of pressure sensitive tape may be applied to secure the exposed end 19 of the body of the rolled diaper. Neither of the later securing means are absolutely essential since the diaper will tend to hold the rolled shape shown in FIG. 4 and even if it unrolls to some extent little, if any, odor will escape from the diaper pad itself. Obviously, the tighter the roll is maintained the less vapor will escape.

If the diaper structure of FIG. 2a is used, it would be refolded after use into the cross sectional configuration shown in FIG. 2a and then folded upon itself in the manner shown in FIG. 4 to form the closed used diaper package 41.

Figure 5:
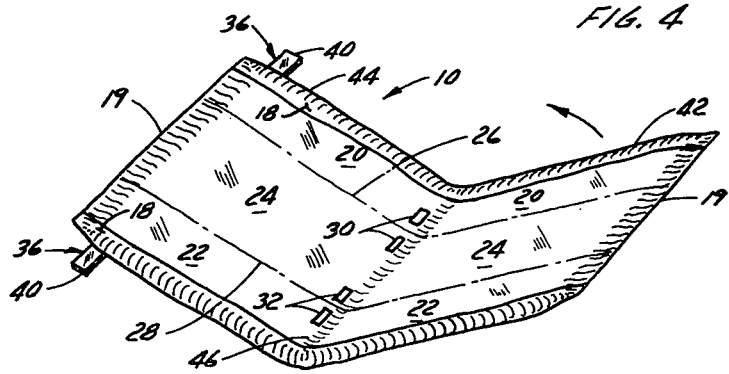
FIGS. 5, 6 and 7 schematically illustrate a preferred method of closing the diaper after use.
Figure 6:
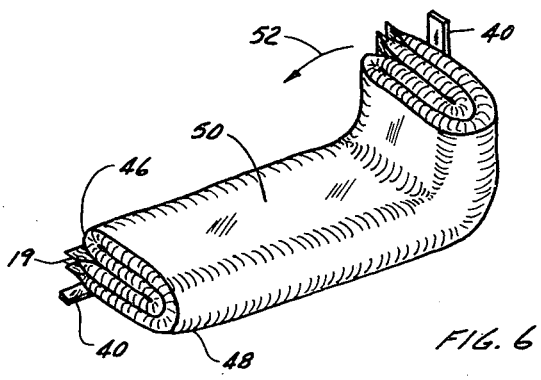
Figure 7:
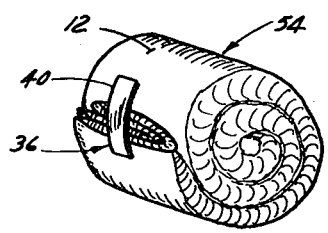

The preferred method of closing a diaper after use is illustrated in FIG. 5, 6 and 7. The method preferably re-uses the tape fasteners and thus when the diaper is to be removed from the child, the free ends 40 of the fasteners 36 are preferably peeled from the backing sheet so that at least one is available for re-use. The diaper is first completely opened up by separating the tack points 30 and 32 so that a substantially flattened pad or sheet is obtained. This sheet is then folded upon itself as indicated in FIG. 5 on a fold line 46 extending transversely of the diaper and dividing the diaper into essentially two equal parts 42 and 44 with the part 44 remote from the tabs 40 being folded onto the part 44 so that the facing sheet 14 on these two parts is in face-to-face relationship. The diaper is then folded on a second fold 48 substantially parallel to the first fold 46 (see FIG. 6) to form an elongated diaper strip 50 substantially as illustrated in FIG. 6. This diaper strip is then rolled upon itself as indicated by the arrow 52 from one end or the other and formed into a compact bundle or used diaper package as illustrated at 54 in FIG. 7 and the exposed free end 40 of the tape fastener 36 is secured to the outer surface, i.e. the plastic backing 12 to hold the diaper in rolled-up configuration as illustrated. If no tab 36 is provided, the diaper may be held in this configuration by any suitable means as described above with reference to FIG. 4.

It will be noted from FIG. 6 and 7 that the only possible areas for vapor escape from the interior of the diaper is at the ends 19 and since the facing sheet 14 and the backing sheet 12 extend beyond the pad 16 in these areas and are secured together, there is very little likelihood of substantial amounts of odour being released. The exposed side edge secured by the fastener 36 is encircled by plastic, i.e. by the turn-over edge 18 of the diaper so little or no odor will escape from this area. The rolled-up or used diaper package 54 may easily be disposed of in a suitable waste container or the like such as a plastic bag that preferably is closable thereby further eliminating the possibility of odour release. The used diaper package 54 may be left for short periods of time without undue inconvenience or release of odour.

The preferred method of closing the diaper to form the used diaper package 54 may be used not only with the diapers disclosed herein but with other diapers having imperforate backing sheets and preferably incorporating tapes similar to the tapes 36 described hereinabove, for example with diapers such as those described in said Canadian Pat. No. 806,856.

Specific seals have been disclosed for the ends (the facing and backing sheets projecting beyond the pad and sealed together) and sides (flaps 18) of the diaper, but other seals may, if desired, be employed in either or both of these positions.

Modifications may be made without departing from the spirit of the invention as defined in the appended claims.

I claim:

1. A disposable diaper comprising a plastic backing sheet, a porous facing sheet, an absorbent pad interposed between said backing and facing sheets, said backing sheet extending beyond said pad to form a flap on each side of said pad, said flap being folded around the side edge of said pad into overlying relationship with said pad, means for sealing longitudinal end edges of said pad, a pair of longitudinally extending folds dividing said diaper into a central section and a pair of lateral wing sections, one of said pair of lateral wing sections being folded into overlying relationship with said central section with a portion of said facing sheet on said wing section in face-to-face relationship with a portion of said facing sheet on said central section, the other of said pair of lateral wing sections being folded over said one wing section thereby to completely enclose the facing sheet.

2. A diaper as defined in claim 1 wherein said means sealing said longitudinal end edges comprises sections of said facing and backing sheet projecting beyond the opposite longitudinal end edges of said pad, said sections being secured in face-to-face relationship.

3. A diaper structure as defined in claim 1 wherein one of said pair of lateral wing sections is folded back upon itself to form one-half a box pleat.

4. A diaper as defined in claim 2 wherein a crotch region spaced from the longitudinal end edges of said diaper is formed in said diaper by tack points securing said pair of lateral wing sections to said central section in said crotch region.

5. A diaper as defined in claim 3 wherein a crotch region spaced from the longitudinal end edges of said diaper is formed in said diaper by tack points securing said pair of lateral wing sections to said central section in said crotch region.

6. The diaper as defined in claim 4 wherein a volatile substance is contained within said diaper.

* * * * *